United States Patent [19]

Hayashi et al.

[11] 3,953,495

[45] Apr. 27, 1976

[54] 16-METHYLENE PGE$_2$

[75] Inventors: Masaki Hayashi; Seiji Kori, both of Takatsuki; Hajimu Miyake, Suita, all of Japan

[73] Assignee: Ono Pharmaceutical Company, Osaka, Japan

[22] Filed: Aug. 29, 1974

[21] Appl. No.: 501,548

[30] Foreign Application Priority Data

Aug. 31, 1973 United Kingdom............... 41124/73

[52] U.S. Cl.......................... 260/468 D; 260/209 R; 260/343.3 R; 260/346.2 R; 260/480 R; 260/448.8 R; 260/514 D; 260/520 N; 260/535 R; 260/946; 424/305; 424/317

[51] Int. Cl.$^2$.................. C07C 61/38; C07C 64/74
[58] Field of Search...................... 260/468 D, 514 D

[56] References Cited
UNITED STATES PATENTS

| | | | |
|---|---|---|---|
| 3,849,487 | 11/1974 | Ridy..................................... | 260/514 |
| 3,892,795 | 7/1975 | Magerlin............................. | 260/468 |

Primary Examiner—Robert Gerstl
Attorney, Agent, or Firm—Albert H. Graddis; Frank S. Chow

[57] ABSTRACT

The present invention relates to 16-methylene prostaglandins. These compounds are useful as anti-ulcer agents, bronchodilators and so on.

4 Claims, No Drawings

16-METHYLENE PGE$_2$

Prostaglandins are derivatives of prostanoic acid which has the following formula:

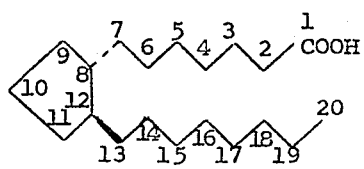

various types of prostaglandins are known, the types depending inter alia on the structure and substituents on the alicyclic ring. For example, the alicyclic rings of prostaglandins F(PGF) and E(PGE) have the structures:

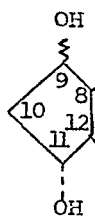 and 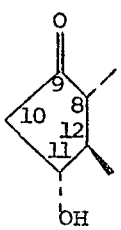

II             III respectively, the wavy line indicating attachment of the hydroxy group in the α- or β-configuration.

Such compounds are sub-classified according to the position of double bond(s) in the side chain(s) attached to the 8- and 12-positions of the alicyclic ring. Thus PG-1 compounds have a trans-double bond between $C_{13}$–$C_{14}$(trans-$\Delta^{13}$), PG-2 compounds have a cis-double bond between $C_5$–$C_6$ and a trans-double bond between $C_{13}$–$C_{14}$(cis-$\Delta^5$, trans-$\Delta^{13}$), and PG-3 compounds have cis-double bonds between $C_5$–$C_6$ and $C_{17}$–$C_{18}$ and a trans-double bond between $C_{13}$–$C_{14}$ (cis-$\Delta^5$, trans-$\Delta^{13}$, cis-$\Delta^{17}$). For example, prostaglandin $F_{1\alpha}$ (PGF$_{1\alpha}$) and prostaglandin $E_1$ (PGE$_1$) are characterized by the following structures IV and V

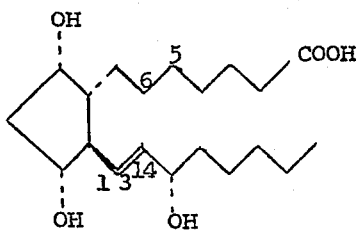

IV and

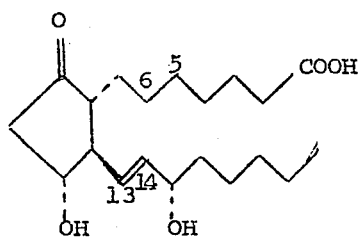

V respectively. The structures of PGF$_{2\alpha}$ and PGE$_2$, as members of the PG-2 group, correspond to those of formulae IV and V respectively with a cis-double bond between the carbon atoms in positions 5 and 6.

Moreover, when one or more methylene groups are added to, or eliminated from, the aliphatic group attached to the 12-position of the alicyclic ring of the prostaglandins the compounds are known, in accordance with the usual rules of organic nomenclature, as ω-homo-prostaglandins (methylene groups added) or ω-nor-prostaglandins (methylene group eliminated) and, when more than one methylene group is added or eliminated, the number is indicated by di-, tri- etc. before the prefix "homo" or "nor".

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

During the past decade widespread investigations have been carried out in order to discover inter alia new products possessing the pharmacological properties of the 'natural' prostaglandins or one or more of such properties to an enhanced degree, or hitherto unknown pharmacological properties. It has now been found that by replacing the hydrogen atoms attached to the carbon atoms in the 16-position of prostaglandins $F_{2\alpha}$ and $E_2$ and certain analogues thereof by a methylene group (=CH$_2$) the pharmacological properties of 'natural' prostaglandins may, in some aspects of their activities, be improved or modified.

The present invention accordingly provides new prostaglandin analogues of the general formula:

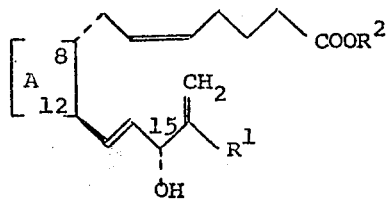

VI (wherein A represents a grouping of the formula:-

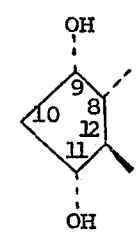 or 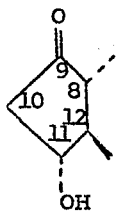

VII           III

, R$^1$ represents a hydrogen atom or a straight- or branched-chain aliphatic hydrocarbon, e.g. alkyl, group containing from 1 to 6 carbon atoms, preferably the n-butyl group, and R$^2$ represents a hydrogen atom or a straight- or branched-chain alkyl group containing from 1 to 12 carbon atoms) and cyclodextrin clathrates thereof and, when R$^2$ represents a hydrogen atom, non-toxic (e.g. sodium) salts thereof.

The present invention is concerned with all compounds of general formula VI in the 'natural' form or its enantiomeric form, or mixtures thereof, more particularly the racemic form consisting of equimolecular mixtures of natural and its enantiomeric form.

As will be apparent to those skilled in the art, the compounds depicted in general formula VI have at least four centres of chirality, these four centres of chirality being at the cyclopentane ring carbon atoms of group A identified as 8 and 12, at the position identified as 11 of the cyclopentane rings in formulae III and VII, and at the C-15 carbon atoms which has attached to it an α-hydroxy group. A further centre of chirality occurs when the group A carries an α-hydroxy group on the carbon atom in position 9 (i.e. when the ring is that of formula VII), and further centres of chirality may occur in aliphatic hydrocarbon groups represented by the symbol R¹. The presence of chirality leads, as is well known, to the existence of isomerism. However, the compounds of general formula VI all have such a configuration that the side-chains attached to the ring carbon atoms in the positions identified as 8 and 12 are trans with respect to each other. Accordingly, all isomers of general formula VI, and mixtures thereof, which have those side-chains attached to the ring carbon atoms in positions 8 and 12 in the trans-configuration and have an α-hydroxy group as depicted in the 15-position are to be considered within the scope of general formula VI.

According to a feature of thee present invention, the prostaglandin analogues of general formula VI, wherein A represents a grouping of formula VII, R¹ is as hereinbefore defined and R² represents a hydrogen atom, are prepared by the process which comprises reacting a bicyclo-octane derivative of the general formula:-

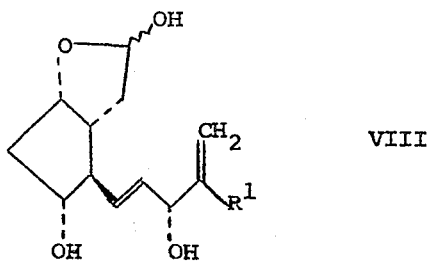

VIII (wherein R¹ is as hereinbefore defined and ∼ indicates attachment of the hydroxy group in α- or β-configuration) with 4-hydroxycarbonyl-n-butylidenetriphenylphosphorane of the formula:

$(C_6H_5)_3P=CH.CH_2.CH_2.CH_2COOH$    IX

The reaction between the bicyclo-octane derivative of general formula VIII and the triphenylphosphorane compound is carried out under the normal conditions utilized for effecting the Wittig reaction, e.g. in an inert solvent. The reaction is preferably carried out in dimethylsulphoxide because the phosphorane compound is practically insoluble in other solvents, e.g. tetrahydrofuran, and because a cis-double bond must be formed stereospecifically in the Wittig reaction. For the better performance of the Wittig reaction, more than four molecular equivalents of the phosphorane compound are required for each mole of the bicyclooctane reactant. The reaction is generally effected at a temperature of 0°–40°C., preferably at 15°–30°C., and is usually complete after about one to five hours at laboratory temperature. The acid product of formula VI may be extracted from the reaction mixture by conventional procedures, the extract concentrated under reduced pressure and the residue further purified by column chromatography on silica gel.

The bicyclo-octane derivatives of general formula VIII may be prepared by the simultaneous reduction and deacetylation of a compound of the general formula:

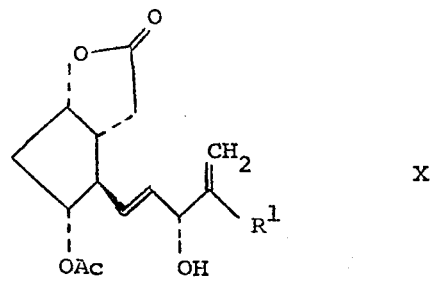

X (wherein R¹ is as hereinbefore defined and Ac represents the acetyl group) by treatment with three molecular equivalents of diisobutylaluminium hydride in toluene at −60°C. for 30 minutes.

The compounds of general formula X may be prepared by the reduction of a compound of the general formula:

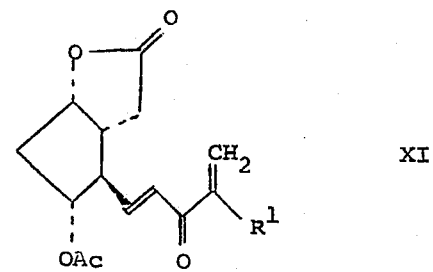

XI (wherein R¹ and Ac are as hereinbefore defined) by treatment with excess sodium borohydride in methanol at a temperature of −40°C. to −30°C. for 20 minutes to give a mixture (ratio about 1:1) of the compound of general formula X and its β-hydroxy epimer. Separation of the desired compound of general formula X from the mixture may be effected by column chromatography on silica gel using a mixture of diethyl ether — ethyl acetate — n-hexane (200:8:15) as eluent.

The compounds of general formula XI may be prepared by the reaction of a compound of the formula:

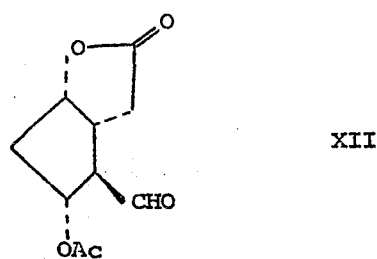

XII (wherein Ac is as hereinbefore defined) with the sodio derivative of a compound of the general formula:

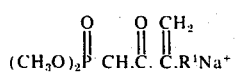

XIII (wherein R[1] is as hereinbefore defined) in tetrahydrofuran at a temperature of 20°C. to 30°C. for 2 hours to form stereospecifically the trans-enone lactone of general formula XI.

The hereinbefore described sequence of reactions for the preparation of the products of the present invention of general formula VI, A representing a group of formula VII, is illustrated schematically in following Chart A, wherein R[1], Ac and ⌇ are as hereinbefore defined.

CHART A.

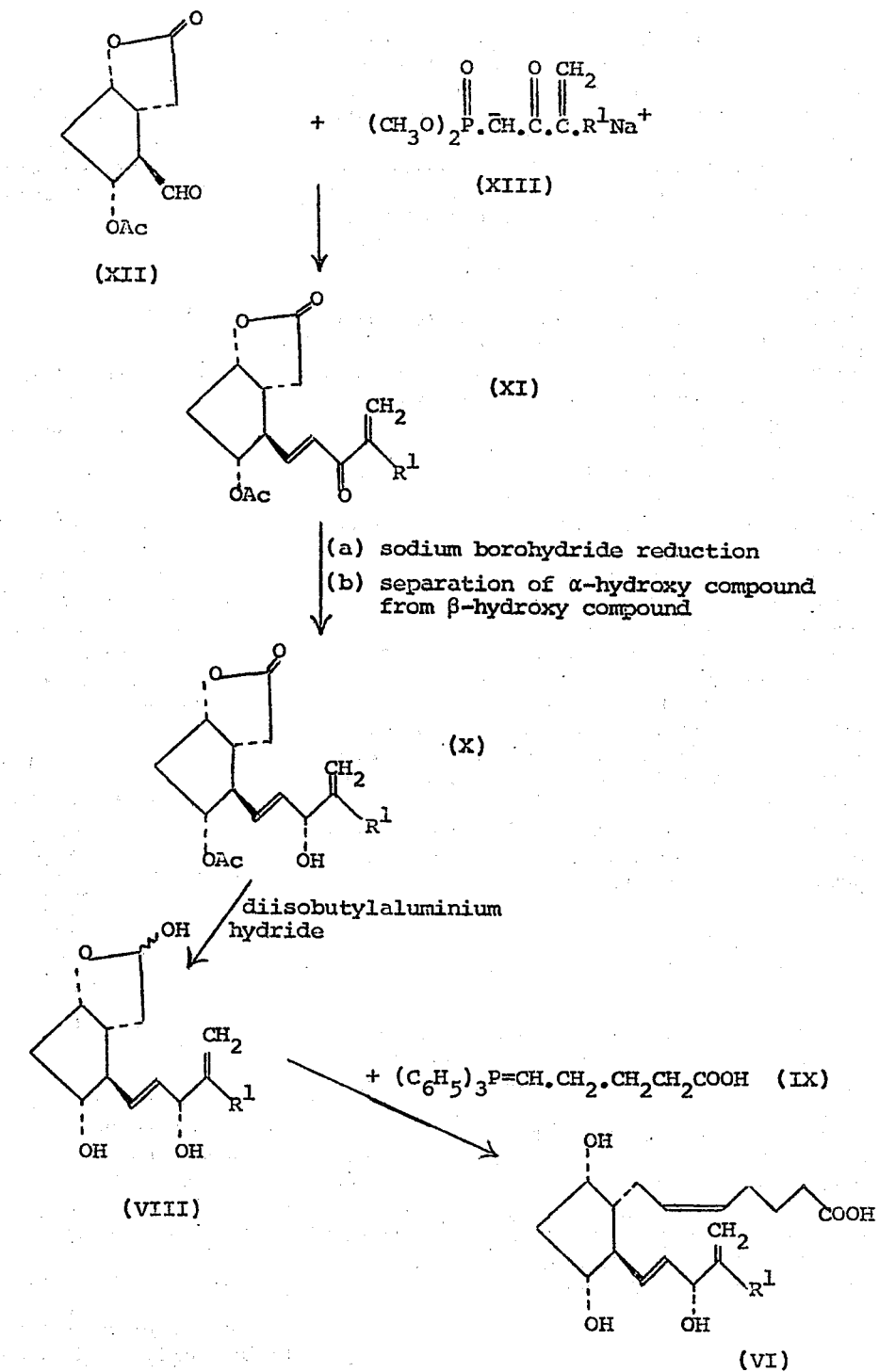

It is to be observed that the compounds of general formula VI, VIII and X are very unstable in the presence of acids because of the presence of the acid-sensitive partial structure

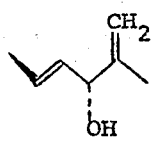

The instability to acid conditions of the compounds of general formula VI renders inapplicable for the preparation of these compounds the general method of Corey as described in the Journal of the American Chemical Society, 92, 397 (1970) whereby a compound of general formula X would be hydrolyzed and the two hydroxy groups thus obtained protected by tetrahydropyranylation by treatment with dihydropyran in the presence of a trace of toluene-p-sulphonic acid to give the corresponding bistetrahydropyranylated analogues of the compound of formula X and a compound of general formula VI having tetrahydropyranyloxy groups in positions 11 and 15 (prepared from the corresponding bistetrahydropyranylated analogue of the compound of formula VIII, itself prepared from the corresponding bistetrahydropyranylated analogue of the compound of formula X) would be used, since the protection of the hydroxy groups by treatment with dihydropyran in the presence of a trace of toluene-p-sulphonic acid and the final stage hydrolysis under acid conditions of the tetrahydropyranyloxy groups of the bistetrahydropyranylated analogue of the compound of formula VI produces compounds having conjugated double bonds in the side-chain rather than the desired bistetrahydropyranylated analogue of the compound of formula X or the desired product of general formula VI.

The compound of formula XII, i.e. 2-oxa-3-oxo-6-syn-formyl-7-anti-acetoxy-cis-bicyclo[3,3,0]octane is a known substance, the preparation of which is described in the Journal of the American Chemical Society, 92, 397 (1970).

The compounds of general formula XIII may be prepared by the dropwise addition of a solution of a compound of the general formula:

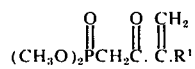  XIV (wherein R¹ is as hereinbefore defined) in tetrahydrofuran to a suspension of sodium hydride in tetrahydrofuran under an atmosphere of nitrogen at laboratory temperature.

The compounds of general formula XIV may be prepared by adding dropwise a 2N solution of n-butyllithium in diethyl ether to a solution of dimethyl methyl phosphonate in tetrahydrofuran under an atmosphere of nitrogen at a temperature of from −50°C. to −60°C. and, after ten minutes, adding dropwise a solution of a compound of the general formula:

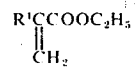  XV (wherein R¹ is as hereinbefore defined) in tetrahydrofuran to the reaction mixture at a temperature of from −65°C. to −70°C. After stirring the reaction mixture for four hours at that temperature and then overnight at 0°C., the desired product of general formula XIV is obtained.

The compounds of general formula XV may be prepared by the esterification of a compound of the general formula:

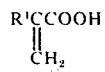  XVI (wherein R¹ is as hereinbefore defined) with ethanol and toluene-p-sulphonic acid in benzene.

The compounds of general formula XVI may be prepared by the method described in the Journal of Organic Chemistry 37, 1256 (1972) from compounds of the general formula:

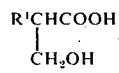  XVII wherein R¹ is as hereinbefore defined.

The compounds of general formula XVII may be prepared from compounds of the general formula:

  XVIII (wherein R¹ is as hereinbefore defined) by the method which is also described in the Journal of Organic Chemistry 37, 1256 (1972).

The hereinbefore described sequence of reactions for the preparation of the compounds of general formula XIII from compounds of general formula XVIII is illustrated schematically in following Chart B, wherein R¹ is as hereinbefore defined.

CHART B

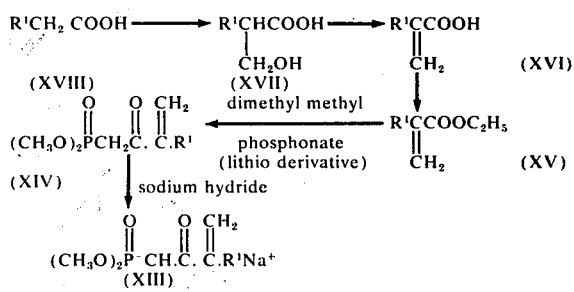

The compound of general formula IX may be prepared by known methods, for example by the procedure described in the Journal of the American Chemical Society, 91, 5675 (1969). Thus, the compound of formula IX may be prepared by reacting a compound of the general formula:

  XIX wherein Z represents a chlorine or bromine atom, e.g. 4-hydroxycarbonyl-n-butyl-triphenylphosphonium bromide, with an alkali metal, e.g. sodium, methylsulphinyl carbanide. The reaction is preferably carried out in an inert solvent, for example dimethylsulphoxide, at ambient temperature. In dimethylsulphoxide, the phosphorane of formula IX is formed within a short time and the product is scarlet. The alkali metal methylsulphinyl carbanide may be prepared in situ by reacting an alkali metal, e.g. sodium, hydride with dimethylsulphoxide at a temperature of from 65° to 70°C.

According to a further feature of the present invention, the compounds of general formula VI, wherein A represents a grouping of formula III and $R^1$ and $R^2$ are as hereinbefore defined, are prepared by the process which comprises hydrolyzing the trimethylsilyloxy groups of a compound of the general formula:

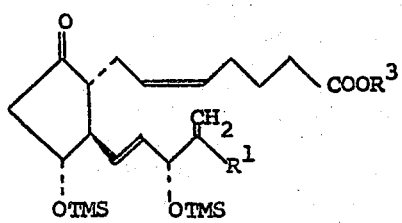

XX (wherein $R^1$ is as hereinbefore defined, $R^3$ represents a straight- or branched-chain alkyl group containing from 1 to 12 carbon atoms, and TMS represents the trimethylsilyl group) to hydroxy groups under extremely mild acidic conditions, for example by treatment with an aqueous oxalic acid solution in the presence of an inert solvent, e.g. ethyl acetate, to give compounds of the general formula:

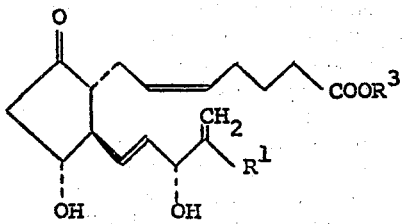

VIA (wherein $R^1$ and $R^3$ are as hereinbefore defined), followed, if desired, by treatment of the ester with bakers' yeast [cf. C. J. Sih et al, Journal of the American Chemical Society, 94, 3643-3644 (1972)] to give a corresponding acid of general formula VI wherein A represents a grouping of formula III, $R^2$ represents a hydrogen atom and $R^1$ is as hereinbefore defined.

The compounds of general formula XX may be prepared by the oxidation of a compound of the general formula:

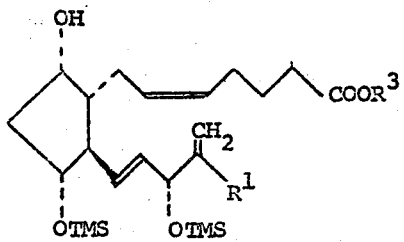

XXI (wherein $R^1$, $R^3$ and TMS are as hereinbefore defined) with Collin's reagent (chromium trioxide in pyridine) in the presence of an inert solvent, e.g. methylene chloride, preferably at a temperature of about 10°C.

The compounds of general formula XXI may be prepared by the reaction of a compound of the general formula:

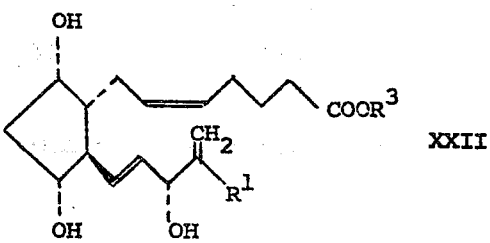

XXII (wherein $R^1$ and $R^3$ are as hereinbefore defined) with N-trimethylsilyldiethylamine or N,O-bis(trimethylsilyl)-acetamide in acetone, preferably at a temperature of about 30°C.

The compounds of general formula XXII may be prepared from the corresponding acids of general formula VI, wherein A represents a grouping of formula VII, $R^1$ is as hereinbefore defined and $R^2$ represents a hydrogen atom (themselves prepared by the procedures hereinbefore described) by known methods for the esterification of carboxylic acids, for example by the application of methods later described herein for the preparation of compounds of general formula VI wherein $R^2$ represents an alkyl group and the other symbols are as hereinbefore defined.

The hereinbefore described sequence of reactions for the preparation of compounds of general formula VI, wherein A represents a grouping of formula III and $R^1$ and $R^2$ are as hereinbefore defined, is illustrated schematically in following Chart C, wherein $R^1$, $R^3$ and TMS are as hereinbefore defined.

CHART C

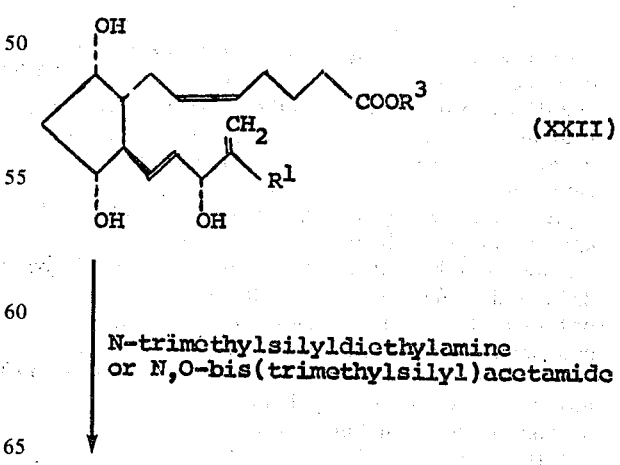

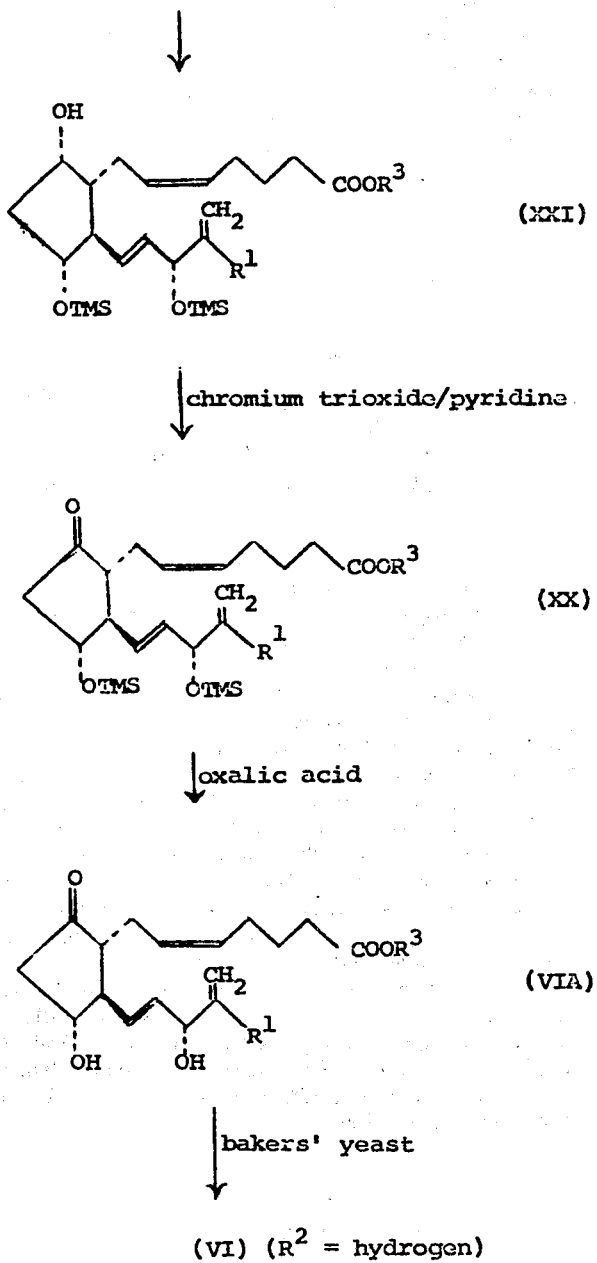

According to a further feature of the present invention, the compounds of general formula VI, wherein A and $R^1$ are as hereinbefore defined and $R^2$ represents a straight- or branched-chain alkyl group containing from 1 to 12 carbon atoms, are prepared by the esterification of corresponding acids of formula VI wherein $R^2$ represents a hydrogen atom by reaction with (i) the appropriate diazoalkane in an inert organic solvent, e.g. diethyl ether, at a temperature of from $-10°$ to $25°C$. and preferably $0°C$., (ii) the appropriate alcohol or thiol in the presence of dicyclohexylcarbodiimide as condensing agent, or (iii) the appropriate alcohol following formation of a mixed anhydride by adding a tertiary amine and pivaloyl halide or an arylsulphonyl or alkylsulphonyl halide (cf. our Belgian Pat. Nos. 775,106 and 776,294).

Compounds of general formula VI wherein $R^2$ represents a hydrogen atom may, if desired, be converted by known methods into non-toxic salts.

By the term "non-toxic salts", as used in this specification, is meant salts the cations of which are relatively innocuous to the animal organism when used in therapeutic doses so that the beneficial pharmacological properties of the compounds of general formula VI are not vitiated by side-effects ascribable to those cations. Preferably the salts are water-soluble. Suitable salts include the alkali metal, e.g. sodium and potassium, and ammonium salts and pharmaceutically-acceptable (i.e. non-toxic) amine salts. Amines suitable for forming such salts with carboxylic acid are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms.

The non-toxic salts may be prepared from compounds of general formula VI wherein $R^2$ represents a hydrogen atom by known methods, for example by reaction of stoichiometric quantities of compounds of general formula VI and the appropriate base, e.g. an alkali metal hydroxide or carbonate, ammonium hydroxide, ammonia or an amine, in a suitable solvent. The salts may be isolated by lyophilisation of the solution or, if sufficiently insoluble in the reaction medium, by filtration, if necessary after removal of part of the solvent.

Cyclodextrin clathrates of compounds of general formula VI may be prepared by dissolving the cyclodextrin in water and/or an organic solvent which is miscible with water and adding to the solution the compound of general formula VI in a water-miscible organic solvent. The mixture is then heated and the desired cyclodextrin clathrate product isolated by concentrating the mixture under reduced pressure or by cooling and separating the product by filtration or decanting. The ratio of organic solvent to water may be varied according to the the solubilities of the starting materials and products. Preferably the temperature is not allowed to exceed $70°C$. during the preparation of the cyclodextrin clathrates. $\alpha$-, $\beta$- or $\gamma$-Cyclodextrins or mixtures thereof may be used in the preparation of the cyclodextrin clathrates. Conversion into their cyclodextrin clathrates serves to increase the stability of the compounds of general formula VI.

By the term 'known methods' as used in the present specification is meant methods heretofore used or described in the chemical literature.

The prostaglandin analogues of general formulae XX and XXI employed as starting materials for the preparation of 16-methylene-$PGE_2$ compounds are themselves new and, as such, constitute a further feature of the invention.

The new prostaglandin compounds of the present invention and their cyclodextrin clathrates and non-toxic salts, possess the valuable pharmacological properties typical of prostaglandins in a selective fashion including, in particular, luteolytic activity, stimulatory activity on uterine contraction and antinidatory activity in female mammals, hypotensive activity, inhibitory activity on gastric acid secretion and gastric ulceration, bronchodilator activity and stimulatory activity on intestinal contraction and are useful in the control of oestrus in female mammals, in particular in economically valuable domestic animals, e.g. ewes, mares and cows, for example, in order to facilitate artificial insemination, in the induction of labour in pregnant female mammals, including economically valuable domestic animals, e.g. ewes, mares, cows and sows, in the procurement of abortion in pregnant female mammals, in the prevention of pregnancy in female mammals, including bitches, in the treatment of hypertension, in the treatment of gastric ulceration, in the treatment of asthma, in the treatment of intestinal dyskinesia and post-operative intestinal paralysis and in the prevention and treatment of constipation. The compounds of this invention induce moderate cutaneous inflammation upon topical application to the skin. This topical activity may be indicated in the management of chronically recurrent skin diseases which may respond to induced inflammation. In particular 16-methylene-PGF$_{2\alpha}$ is of value in the control of oestrus in female mammals and in the induction of labour in pregnant female mammals, 16-methylene-PGF$_{2\alpha}$ and 16-methylene-PGF$_{2\alpha}$ methyl ester are of value in the prevention of pregnancy in female mammals, 16-methylene-PGE$_2$ methyl ester is of value in the prevention of pregnancy and in the control of oestrus in female mammals, and in the treatment of hypertension, gastric ulceration and asthma, and 16-methylene-PGF$_{2\alpha}$ and 16-methylene-PGE$_2$ methyl ester are of value in the treatment of intestinal dyskinesia and post-operative intestinal paralysis and in the prevention and treatment of constipation. For example in laboratory screening tests:

a. 16-methylene-PGF$_{2\alpha}$ produces luteolysis in rats which were hysterectomized on the Day 5 of gestation, the day when the presence of sperm in the vagina was confirmed being regarded as Day 0 of gestation. The test compound or saline (as control) was administered from the second day following the hysterectomy until the first oestrus began. The luteal period was observed by the vaginal smear test. The following results were obtained:-

| Dose | | Luteal Period (days) | Efficacy |
| --- | --- | --- | --- |
| Control (Saline) | (b.i.d.) | 16.7±0.7 | 0% |
| 16-Methylene-PGF$_{2\alpha}$ | 2.5µg./kg. (b.i.d.) | 7.3±1.0 | 28.6% |
| | 5µg./kg. (b.i.d.) | 4.6±0.4 | 87.7% |
| [Natural PGF$_{2\alpha}$ | 50µg./kg. (b.i.d.) | 8.4±2.5 | 60%] | b. 16-methylene-PGF$_{2\alpha}$ produces uterine contractions:

i. In vitro The isolated uterus from the overiectomized rat was placed in a bath of low calcium ion Lock-Ringer solution; 16-methylene-PGF$_{2\alpha}$ was added to the bath and caused a 50% contraction at a concentration of 7.8 ng./ml. Natural PGF$_{2\alpha}$ caused 50% contraction at a concentration of 4.2 ng./ml.

ii. In vivo A small balloon was inserted into the uterus of the rat at the 15th day of gestation and the intrauterine pressure measured by means of a polygraph. The effective dose of 16-methylene-PGF$_{2\alpha}$ in inducing uterine contraction, as determined by the effect on intrauterine pressure, was 21.3±10.10 µg./kg. (Mean±S. E.) by intravenous administration. The corresponding effective dose of natural PGF$_{2\alpha}$ was 22.4±1.66 µg./kg.

c. 16-methylene-PGF$_{2\alpha}$ produces an antinidatory effect on the pregnant rat at a dose 500 µg./kg. when administered subcutaneously;

d. 16-methylene-PGF$_{2\alpha}$ methyl ester produces an antinidatory effect on the pregnant rat at doses of 500–1000 µg./kg. when administered subcutaneously;

e. 16-methylene-PGE$_2$ methyl ester produces luteolysis in 50% of pregnant hamsters, treated on Day 4 of gestation and killed on Day 7, at a dose of 0.25 mg./kg. administered subcutaneously, the comparable doses of natural PGE$_2$ being 1.0 mg./kg.;

f. 16-methylene-PGE$_2$ methyl ester produces (i), when administered intravenously to the allobarbitalanaesthetized dog, falls in blood pressure of 18 mm.Hg, 29 mm.Hg and 38 mm.Hg lasting 12 minutes, 14 minutes and 17 minutes respectively at doses of 0.02 µg./kg., 0.05 µg./kg. and 0.1 µg./kg. respectively, while when similarly administered, PGE$_2$ produces falls in blood pressure of 18 mm.Hg., 34 mm.Hg and 52 mm.Hg lasting 6 minutes, 6 minutes and 19 minutes respectively at doses of 1 µg./kg., 2 µg./kg. and 5 µg./kg. respectively, (ii) when administered orally to the allobarbital-anaesthetized dog, falls in blood pressure of 17 mm.Hg and 45 mm.Hg lasting 40 minutes and 60 minutes respectively at doses of 20 µg./kg. and 50 µg./kg. respectively, and (iii) when administered orally to the conscious hypertensive rat, a fall of 32.3 mm.Hg one hour after treatment at a dose of 2 mg./kg.;

g. in gastric stress ulceration in rats produced according to the method of Takagi and Okabe [Jap. J. Pharmac. 18, 9-18 (1968)], 16-methylene-PGE$_2$ methyl ester produces a 36.63% inhibition of stress ulceration when administered orally in two doses of 20µg./kg. each and a 62.62% inhibition of stress ulceration when administered orally in two doses of 50 µg./kg. each to rats soaked in a water bath at 22°C. for 8 hours, and 75.31% and 84.62% inhibitions of stress ulceration when administered orally at doses of 50µg./kg. and 100 µg./kg. respectively, to rats soaked in a water bath at 19°C. for 6 hours;

h. in gastric ulceration produced in Wistar strain male rats, weighing 200–230 g., by the oral administration of 20 mg./kg. of indomethacin after starvation for 24 hours, 16-methylene-PGE$_2$ methyl ester administered in a single dose of 1 µg./kg. and 5 µg./kg. respectively, 10 minutes before the administration of indomethacin, produced inhibitions of 69.2% and 87.8%, respectively, of gastric ulceration as determined by examination of the number and size of ulcers 6 hours after the oral administration of indomethacin, i. against the increase in the resistance in the respiratory tract of the guinea pig induced by the intravenous administration of histamine (10–15 µg./kg.), as determined by the method of Konzett and Rossler [Arch, exp. Path. Pharmak. 195, 71–74 (1940)], 16-methylene-PGE$_2$ methyl ester produces inhibitions of 48.7% and 54.6% at doses of 0.05 µg./kg. and 0.1 µg./kg. respectively by intravenous adminstration, being 18.9 and 14.4 times as potent, respectively, as $PGE_1$ at these doses and exhibiting a longer duration of activity than $PGE_1$, j. 16-methylene-$PGE_2$ methyl ester produces 100% inhibition of pentagastrin (2 μg./kg./hr., i.v.) induced gastric acid secretion in 50% of anaesthetized rats when used at a dose of 0.14 μg./body/min. and administered orally, k. when the time taken for convulsion to occur in conscious guinea pigs exposed to a histamine-containing aerosol was determined and, a few days later, the animals were again exposed to the histamine-containing aerosol, 90 seconds after the administration of an aerosol containing 16-methylene-$PGE_2$ methyl ester or one hour after the oral adminstration of 16-methylene-$PGE_2$ methyl ester, 16-methylene-$PGE_2$ methyl ester increases the pre-convulsion time by 51%, 82%, 156%, 130% and 167% when administered as an aerosol generated from solutions containing 0.3 μg./ml., 0.5μg./ml., 0.7 μg./ml., 1.0 μg./ml. and 3.0 μg./ml., respectively, and, when administered orally, increases the pre-convulsion time from 118.0±13.9 seconds to 156.0±28.9 seconds and from 108.0±8.0 seconds to 232.0±32.0 seconds at doses of 50 μg./kg. and 100 μg./kg. respectively, while $PGE_1$ increases the pre-convulsion time by 27%, 80%, 131% and 189% when administered as an aerosol generated from solutions containing 0.5 μg./ml., 1.0 μg./ml., 5.0 μg./ml. and 10.0 μg./ml., respectively, and, when administered orally, increases the pre-convulsion time from 105±9.6 seconds to 125.0±15.0 seconds at a dose of 100 μg./kg.;

l. on isolated guinea pig tracheal muscle, the administration of 16-methylene-$PGE_2$ methyl ester, when maximum histamine-induced contraction had been produced, gives a relaxant activity ($PD_2$) of 7.11±0.21 calculated according to the method of Rossum et al [Arch. Int. Pharmacodyn. Ther. 143, 299 (1963)], the $PD_2$ value being the negative logarithm of the gram concentration of the compound producing 50% relaxation of the tracheal muscle.

m. 16-methylene-$PGF_{2\alpha}$ was administered intaperitoneally to ICR-strain female mice. The $ED_{50}$ in producing diarrhoea was 45 μg./kg. The corresponding $ED_{50}$ for natural $PGF_{2\alpha}$ was 220 μg./kg.

n. 16-methylene-$PGE_2$ methyl ester was administered orally to mice. The $ED_{50}$ in producing wet faeces was 1.07 mg./kg. The corresponding $ED_{50}$ for natural $PGE_2$ was 5.8 mg./kg.

o. 16-methylene-$PGF_{2\alpha}$ was administered by intravenous injection over 15 seconds into ICR-strain female mice. The number of deaths during the next seven days was observed. The acute $LD_{50}$ for 16-methylene-$PGF_{2\alpha}$, calculated by the Litchfield-Wilcoxon method, was >100 mg./kg. The corresponding $LD_{50}$ for natural $PGF_{2\alpha}$ was 56 mg./kg.

p. when administered orally to dogs, 16-methylene-$PGE_2$ methyl ester did not produce diarrhoea at a dose of 50 μg/kg. [In (a) to (p) above, doses of test compound are expressed in terms of weight of test compound per kilogramme of animal body weight].

It is to be observed that the new prostaglandin compounds of the present invention and their cyclodextrin clathrates and non-toxic salts stimulate intestinal contraction and produce moistening of the faeces and diarrhoea only at doses substantially higher that the doses which are required to produce the other valuable pharmacodynamic effects hereinbefore described and hence selectively of action in this respect may be achieved by suitable selection of dosages.

The following Examples and Reference Examples illustrate the process of the present invention and products thereof. In the Examples 'IR', 'NMR' and 'TLC' represent, respectively, 'Infrared absorption spectrum', 'Nuclear magnetic resonance spectrum' and 'Thin layer chromatography'.

REFERENCE EXAMPLE 1

Synthesis of ethyl 2-n-butylacrylate 2-n-Butylacrylic acid (26 g.), ethanol (30 ml.), toluene-p-sulphonic acid (3 g.) and hydroquinone (260 mg.) were dissolved in thiophene-free benzene (350 ml.). The solution was heated under reflux with stirring and the resulting water was removed from the reaction system.

After the reaction was complete, the reaction mixture was diluted with diethyl ether and washed with aqueous sodium bicarbonate solution, water and saturated aqueous sodium chloride solution. The solution was dried over magnesium sulphate and concentrated in vacuo. The residue was distilled under reduced pressure to give pure ethyl 2-n-butylacrylate (24 g.; 76%), b.p. 77°C/21 mm Hg., having the following physical characteristics:-

IR (liquid film): 1715, 1630 $cm^{-1}$.

NMR (chloroform deuteride solution):

δ: 6.03 (1H, singlet), 5.42 (1H, singlet), 4.10 (2H, quartet), 2.45–1.94 (2H, triplet).

REFERENCE EXAMPLE 2

Synthesis of dimethyl 2-oxo-3-methylene-n-heptylphosphonate

A 2N solution (400 ml.) of n-butyllithium in diethyl ether was added dropwise to a solution of dimethyl methyl phosphonate (110 g.) in pure anhydrous tetrahydrofuran (700 ml.) with stirring under nitrogen, while the reaction temperature was kept within the range of −50° to −60°C. After ten minutes, a solution of ethyl 2-n-butylacrylate (prepared as described in Reference Example 1; 60 g.) in tetrahydrofuran (150 ml.) was added dropwise to the reaction mixture at −65° to −70°C and stirred for four hours at the same temperature. The reaction mixture was further stirred overnight at 0°C, acidified with acetic acid and concentrated under reduced pressure. Diethyl ether and water were added to the residue in order to remove the water soluble materials. The ethereal solution was dired over magnesium sulphate and concentrated. The residue was distilled under reduced pressure to give pure dimethyl 2-oxo-3-methylene-n-heptylphosphonate (67 g.; 69%), b.p. 100°–125°C/0.1 mm Hg, having the following physical characteristics:

IR (liquid film): 1730, 1675, 1630 $cm^{-1}$.

NMR (chloroform deuteride solution):

δ: 6.18 (1H, singlet), 4.92 (1H, singlet), 3.73 (6H, doublet), 3.90 (2H, doublet), 2.55–2.04 (2H, triplet).

REFERENCE EXAMPLE 3

Synthesis of
2-oxa-3-oxo-6-syn-(3-oxo-4-methylene-oct-trans-1-enyl)-7-anti-acetoxy-cis-bicyclo[3,3,0]octane A solution of dimethyl 2-oxo-3-methylene-n-heptylphosphonate (prepared as described in Reference Example 2; 12 g.) in pure, anhydrous tetrahydrofuran (30 ml.) was added dropwise to a suspension of sodium hydride (0.96 g.) in pure anhydrous tetrahydrofuran (300 ml.) with stirring under nitrogen at laboratory temperatue. After the solution became clear, a solution of 2-oxa-3-oxo-6-syn-formyl-7-anti-acetoxy-cis-bicyclo[3,3,0]octane (12.7 g.) in pure anhydrous tetrahydrofuran (200 ml.) was added dropwise. The reaction mixture was stirred for 2 hours at 20° to 30°C, acidifed with acetic acid and filtered through a pad of silica gel. The filtrate was concentrated under reduced pressure. The residue was subjected to column chromatography on silica gel (1000 g.) using benzeneethyl acetate (4:1) as eluent to give pure 2-oxa-3-oxo-6-syn-(3-oxo-4-methylene-oct-trans-1-enyl)-7-antiacetoxy-cis-bicyclo[3,3,0]octane (6.7 g; 52%), having the following physical characteristics:

IR: 2950, 2925, 2860, 1775, 1740, 1665, 1615, 1420, 1370, 1240, 1175, 1110, 1075, 985 cm$^{-1}$.

NMR (chloroform deuteride solution):

δ: 6.85–6.65 (2H, multiplet), 5.98 (1H, singlet) 5.81 (1H, singlet), 5.30–4.85 (2H, multiplet) 2.02 (3H, singlet), 0.90 (3H, triplet)

TLC (silica gel, benzene-ethyl acetate=4:1): Rf=0.49.

REFERENCE EXAMPLE 4

Synthesis of
2-oxa-3-oxo-6-syn-(3α-hydroxy-4-methylene-oct-trans-1-enyl)-7-anti-acetoxy-cis-bicyclo[3,3,0]-octane Sodium borohydride (2.4 g.) was added dropwise to a solution of 2-oxa-3-oxo-6-syn-(3-oxo-4-methylene-oct-trans-1-enyl)-7-anti-acetoxy-cis-bicyclo[3,3,0]-octane (prepared as described in Reference Example 3; 6.7 g.) in methanol (100 ml.) with stirring at −40° to −30°C. After 20 minutes, the reaction mixture was acidified with acetic acid, concentrated and the residue was extracted with ethyl acetate. The extracts were washed with aqueous sodium bicarbonate solution and saturated aqueous sodium chloride solution. The ethyl acetate solution was concentrated under reduced pressure and the residue was subjected to column chromatography on silica gel (350 g.) using diethyl ether-ethyl acetate-n-hexane (200:8:15) as eluent to give pure 2-oxa-3-oxo-6-syn-(3α-hydroxy-4-methylene-oct-trans-1-enyl)-7-antiacetoxy-cis-bicyclo[3,3,0]octane (1.8 g.; 26.8%), having the following physical characteristics:

IR (liquid film); 3450, 2960, 2930, 2850, 1765, 1735, 1415, 1365, 1240, 1170, 1070-1030, 970, 900 cm$^{-1}$.

NMR (chloroform deuteride solution):

δ: 5.80-5.55 (2H, multiplet), 5.35–4.75 (2H, multiplet), 5.10 (1H, singlet), 4.90 (1H, singlet), 4.70–4.45 (1H, multiplet), 2.03 (3H, singlet), 0.90 (3H, triplet).

TLC (silica gel, dichloromethane-methanol=19:1); Rf=0.57.

[1.1g. of pure 3β-isomer and 1.34 g. of a mixture of the 3α- and 3β-isomers were also obtained]

REFERENCE EXAMPLE 5

Synthesis of
2-oxa-3-hydroxy-6-syn-93α-hydroxy-4-methylene-oct-trans-1-enyl)-7-anti-hydroxy-cis-bicyclo[3,3,0]octane A solution of diisobutylaluminium hydride (4.3 g.) in toluene (20 ml.) was added dropwise to a solution of 2-oxa-3-oxo-6-syn-(3α-hydroxy-4-methylene-oct-trans-1-enyl)-7-anti-acetoxy-cis-bicyclo[3,3,0]-octane (prepared as described in Reference Example 4; 1.7 g.) in toluene (80 ml.) under nitrogen with stirring at −60°C. The reaction mixture was then stirred for 30 minutes and methanol (10 ml.) was added. The reaction temperature was elevated to laboratory temperature and water (30 ml.) was added with stirring. The reaction mixture was filtered to remove the resulting crystalline materials and the filtrate was concentrated to give 2-oxa-3-hydroxy-6-syn-(3α-hydroxy-4-methylene-oct-trans-1-enyl)-7-anti-hydroxy-cis-bicyclo[3,3,0]-octane (1.28 g.; 86%) having the following physical characteristics:

IR (liquid film): 3350, 2950, 2920, 2860, 1650, 1495, 1450, 1380, 1340, 1290, 1250, 1220, 1105, 1070, 1010, 975, 910 cm$^{-1}$.

NMR (chloroform deuteride solution):

5.80–5.35 (2H, multiplet), 5.10 (1H, singlet), 4.85 (1H, singlet), 4.75–4.30 (2H, multiplet), 4.30–3.55 (2H, multiplet), 0.90 (3H, triplet).

TLC (silica gel, dichloromethane-methanol=19:1): Rf=0.27.

EXAMPLE 1

Synthesis of 16-methylene-prostaglandin $F_{2\alpha}$

Sodium hydride (480 mg.) was added to anhydrous dimethyl sulphoxide (10 ml.) and the mixture was stirred with heating at 65° to 70°C for about one hour to obtain sodiomethyl sulphinyl carbanide. The product was allowed to cool to room temperature and then added dropwise to a solution of 4-hydroxycarbonyl-n-butyl-triphenylphosphonium bromide (5.1 g.) in pure anhydrous dimethyl sulphoxide (15 ml.) under nitrogen at 15° to 18°C.

The solution became scarlet in the middle of the addition. Then the mixture was stirred vigorously together with a solution of 2-oxa-3-hydroxy-6-syn-(3α-hydroxy-4-methylene-oct-trans-1-enyl)-7-anti-hydroxy-cis-bicyclo[3,3,0]octane (prepared as described in Reference Example 5; 610 mg.) in pure anhydrous dimethyl sulphoxide (15 ml.) at laboratory temperature for two hours. The reaction mixture was poured into ice-water (500 ml.) and the neutral substance was removed by extraction with an ethyl acetate-diethyl ether (1:1) mixture. The aqueous layer was acidified to pH 3.0 with saturated aqueous oxalic acid solution and extracted with ethyl acetate. The extract was washed with water and saturated aqueous sodium chloride solution. The ethyl acetate solution was dried over sodium sulphate and concentrated under reduced pressure. Ethyl acetate was added to the residue and the solution was filtered to remove the resulting crystalline materials. The filtrate was concentrated under reduced pressure. The residue was subjected to column chromatography on silica gel (50 g.) using a chloroform-tetrahydrofuran (5:1) mixture and ethyl acetate as eluents to obtain crude 16-methyleneprostaglandin $F_{2\alpha}$ (407 mg.). The crude material was subjected again to column chromatography on silica gel (20 g.)

using an ethyl acetate-cyclohexane (5:3) mixture as eluent to obtain pure 16-methyleneprostaglandin $F_{2\alpha}$ (252 mg.; 31.8%), having the following physical characteristics:

IR (liquid film): 3450, 3000, 2960, 2930, 2860, 1710, 1450–1400, 1245, 1200, 1120, 1090, 1055, 1030, 975, 910 cm$^{-1}$.

NMR (acetone deuteride solution):
δ: 5.72–5.50 (2H, multiplet), 5.50–5.25 (2H, multiplet), 5.13 (1H, singlet), 4.95 (4H, broad singlet), 4.89 (1H, singlet), 4.65–4.47 (1H, multiplet), 4.30–4.08 (1H, multiplet), 4.08–3.80 (1H, multiplet), 0.92 (3H, triplet).

TLC (silica gel, chloroform-tetrahydrofuran-acetic acid=10:2:1): Rf=0.16. specific rotation (ethanol solution, c=1.06): $[\alpha]_D^{23} = -11.3°$

EXAMPLE 2

Synthesis of 16-methylene-prostaglandin $F_{2\alpha}$ methyl ester

A solution of 16-methylene-prostaglandin $F_{2\alpha}$ (prepared by the procedure described in Example 1; 500 mg.) in diethyl ether (10 ml.) was cooled to 0°C and maintained at that temperature while an excess of diazomethane in diethyl ether was added until bubbles ceased to evolve. The solution was then kept at 0°C for 10 minutes, the ether evaporated and the residue subjected to column chromatography on silica gel using an ethyl acetate-cyclohexane (2:3) mixture as eluent to give 16-methylene-prostaglandin $F_{2\alpha}$ methyl ester (425 mg.; 79,6%) having the following physical characteristic:

TLC (silica gel, chloroform-tetrahydrofuran-acetic acid = 10:2:1): Rf = 0.36.

EXAMPLE 3

Synthesis of 11,15-bis-trimethylsilyl-16-methyleneprostaglandin $F_{2\alpha}$ methyl ester a. N-Trimethylsilyldiethylamine (1.93 ml.; 10 m.mole) was added, under an atmosphere of nitrogen, to a solution of 16-methylene-prostaglandin $F_{2\alpha}$ methyl ester (prepared as described in Example 2; 380 mg.; 1 m. mole) in dry acetone (20 ml.) and the reaction mixture was stirred for 4 hours at 30°C. The acetone was then evaporated and the residue subjected to column chromatography on silica gel using a cyclohexane-ethyl acetate (6:1) mixture as eluent, to give 11,15-bis-trimethylsilyl-16-methylene-prostaglandin $F_{2\alpha}$ methyl ester (390 mg.; 74.5%) having the following physical characteristic:

TLC (silica gel, cyclohexane-ethyl acetate = 2:1): Rf = 0.74 b. N,O-Bis(trimethylsilyl)acetamide (0.21 ml.; 9.2 m.mole) was added, under an atmosphere of nitrogen, to a solution of 16-methylene-prostaglandin $F_{2\alpha}$ methyl ester (prepared as described in Example 2; 35 mg.; 0.92 m.mole) in dry acetone (2 ml.) and the reaction mixture was stirred for 5 hours at 30°C. The acetone was then evaporated and the residue subjected to column chromatography on silica gel using a cyclohexane-ethyl acetate (6:1) mixture as eluent, to give 11,15-bistrimethylsilyl-16-methylene-prostaglandin $F_{2\alpha}$ methyl ester (34.3 mg.; 71%), identical to the product of (a) above.

EXAMPLE 4

Synthesis of 11,15-bis-trimethylsilyl-16-methylene prostaglandin $E_2$ methyl ester Dry pyridine (1.2 ml.) and chromium trioxide (600 mg.) were added to dry methylene chloride (40 ml.) and the mixture was stirred for 20 minutes at laboratory temperature. Celite (3 g.) was then added. The mixture was cooled to 10°C and maintained at that temperature while a mixture of 11,15-bis-trimethylsilyl-16-methyleneprostaglandin $F_{2\alpha}$ methyl ester (prepared as described in Example 3; 238 mg.; 0.455 m.mole) and dry methylene chloride (10 ml.) was added. After stirring for 10 minutes, isopropanol (1 ml.) was added and the mixture was stirred for a further 10 minutes. NaHSO$_4$·H$_2$O (3 g.) was then added and stirring continued for a further 10 minutes. The reaction mixture was then filtered through a sintered glass filter covered with magnesium sulphate. The filtrate was concentrated and subjected to column chromatography on silica gel using a cyclohexane-ethyl acetate (6:1) mixture as eluent, to give 11,15-bis-trimethylsilyl-16-methylene-prostaglandin $E_2$ methyl ester (153 mg.; 65%), having the following physical characteristic:

TLC (silica gel, cyclohexane-ethyl acetate = 5:1): Rf = 0.49.

EXAMPLE 5

Synthesis of 16-methylene-prostaglandin $E_2$ methyl ester

Saturated aqueous oxalic acid solution (10 ml.) was added to a solution of 11,15-bis-trimethylsilyl-16-methylene prostaglandin $E_2$ methyl ester (prepared as described in Example 4; 150 mg.; 0.287 m.mole) in ethyl acetate (30 ml.). After vigorous stirring for 5 minutes at laboratory temperature, the mixture was transferred to a separating funnel and washed with water followed by saturated aqueous sodium chloride solution. The organic solution was then dried over sodium sulphate, concentrated and subjected to column chromatography on silica gel using a cyclohexane-ethyl acetate (3:2) mixture as eluent to give 16-methyleneprostaglandin $E_2$ methyl ester (85.5 mg.; 80%) having the following physical characteristic:

TLC (silica gel, chloroform-tetrahydrofuran-acetic acid = 10:2:1): Rf = 0.45.

The present invention includes within its scope pharmaceutical compositions which comprise at least one new therapeutically useful prostaglandin compound according to the present invention, together with a pharmaceutical carrier or coating. In clinical practice the new compounds of the present invention will normally be administered orally, vaginally, rectally, parenterally or topically.

Solid compositions for oral administration include compressed tablets, pills, dispersible powders, and granules. In such solid compositions one or more of the active compounds is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the active substances with or without the addition of diluents or excipients.

Solid compositions for vaginal administration include pessaries formulated in manner known per se and containing one or more of the active compounds.

Solid compositions for rectal administration include suppositories formulated in manner known per se and containing one or more of the active compounds.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may be sterilised, for example, by filtration through a bacteria-retaining filter, by incorporation of sterilising agents in the compositions or by irradiation. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance. The dose employed depends upon the desired therapeutic effect, the route of administration and the duration of the treatment.

In the adult, the doses are generally between 0.01 and 5 mg./kg. body weight by oral administration in the treatment of hypertension, between 0.5 and 100 $\mu$g./kg. body weight by oral administration in the treatment of gastric ulceration, between 0.1 and 50 $\mu$g./kg. body weight by aerosol administration in the treatment of asthma, between 50 and 1000 $\mu$g. per body by intrauterine administration in the prevention of pregnancy, between 0.1 and 10 mg. per body by intravenous infusion in the induction of labour and procurement of abortion in women, between 500 $\mu$g. and 25 mg. per body by intramuscular injection in the control of oestrus, e.g. in ewes, cows and mares, and in the induction of labour in ewes, cows, mares and sows, and between 50 and 1000 $\mu$g. per kg. body weight by oral administration in the treatment of intestinal dyskinesia and post-operative intestinal paralysis and in the treatment and prevention of constipation.

Prostaglandin compounds according to the present invention may be administered orally as bronchodilators by any method known per se for administration by inhalation of drugs which are not themselves gaseous under normal conditions of administration. Thus, a solution of the active ingredient in a suitable pharmaceutically-acceptable solvent, for example water, can be nebulized by a mechanical nebulizer, for example a Wright Nebulizer, to give an aerosol of finely-divided liquid particles suitable for inhalation. Advantageously, the solution to be nebulized is diluted, and aqueous solutions containing from 0.001 to 5 mg., and preferably 0.01 to 0.5 mg., of active ingredient per ml. of solution are particularly suitable. The solution may contain stabilizing agents such as sodium bisulphite and buffering agents to give it an isotonic character, e.g. sodium chloride, sodium citrate and citric acid.

The active ingredients may also be administered orally by inhalation in the form of aerosols generated from self-propelling pharmaceutical compositions. Compositions suitable for this purpose may be obtained by dissolving or suspending in finely-divided form, preferably micronized to an average particle size of less than 5 microns, the active ingredients in pharmaceutically-acceptable solvents, e.g. ethanol, which are co-solvents assisting in dissolving the active ingredients in the volatile liquid propellants hereinafter described, or pharmaceutically-acceptable suspending or dispersing agents, for example aliphatic alcohols such as oleyl alcohol, and incorporating the solutions or suspensions obtained with pharmaceutically-acceptable volatile liquid propellants, in conventional pressurized packs which may be made of any suitable material, e.g. metal, plastics or glass, adequate to withstand the pressures generated by the volatile propellant in the pack. Pressurized pharmaceutically-acceptable gases, such as nitrogen, may also be used as propellants. The pressurized pack is preferably fitted with a metered valve which dispenses a controlled quantity of the self-propelling aerosol composition as a single dose.

Suitable volatile liquid propellants are known in the art and include fluorochlorinated alkanes containing from one to four, and preferably one or two, carbon atoms, for example dichlorodifluoromethane, dichlorotetrafluoroethane, trichloromonofluoromethane, dichloromonofluoromethane and monochlorotrifluoromethane. Preferably, the vapour pressure of the volatile liquid propellant is between about 25 and 65 pounds, and more especially between about 30 and 55 pounds, per square inch gauge at 21°C. As is well-known in the art, volatile liquid propellants of different vapour pressures may be mixed in varying proportions to give a propellant having a vapour pressure appropriate to the production of a satisfactory aerosol and suitable for the chosen container. For example dichlorodifluoromethane (vapour pressure 85 pounds per square inch gauge at 21°C.) and dichlorotetrafluoroethane (vapour pressure 28 pounds per square inch gauge at 21°C.) may be mixed in varying proportions to give propellants havig vapour pressures intermediate between those of two constituents, e.g. a mixture of dichlorodifluoromethane and dichlorotetrafluoroethane in the proportions 38:62 respectively by weight has a vapour pressure of 53 pounds per square inch gauge at 21°C.

The self-propelling pharmaceutical compositions may be prepared by dissolving the required quantity of active ingredient in the co-solvent or combining the required quantity of active ingredient with a measured quantity of suspending or dispersing agent. A measured quantity of this composition is then placed in an open container which is to be used as the pressurized pack. The container and its contents are then cooled below the boiling temperature of the volatile propellant to be used. The required quantity of liquid propellant, cooled below its boiling temperature, is then added and the contents of the container mixed. The container is then sealed with the required valve fitting, without allowing the temperature to rise above the boiling temperature of the propellant. The temperature of the sealed container is then allowed to rise to ambient with shaking to ensure complete homogeneity of the contents to give a pressurized pack suitable for generating aerosols for inhalation. Alternatively, the co-solvent solution of the active ingredient or combination of active ingredient and suspending or dispersing agent is placed in the open container, the container sealed with a valve, and the liquid propellant introduced under pressure.

Means for producing self-propelling compositions for generating aerosols for the administration of medicaments are, for example, described in detail in U.S. Pat. Nos. 2,868,691 and 3,095,355.

Preferably, the self-propelling pharmaceutical compositions according to the present invention contain from 0.001 to 5 mg., and more particularly 0.01 to 0.5 mg.; of active ingredient per ml. of solution or suspension. It is important that the pH of solutions and suspensions used, according to the present invention, to generate aerosols should be kept within the range 3 to 8 and preferable that they should be stored at or below 4°C. to avoid pharmacological deactivation of the active ingredient.

In carrying out the present invention, the means of producing an aerosol for inhalation should be selected in accordance with the physico-chemical properties of the active ingredient.

By the term "pharmaceutically-acceptable" as applied in this specification to solvents, suspending or dispersing agents, propellants and gases is meant solvents, suspending or dispersing agents, propellants and gases which are non-toxic when used in aerosols suitable for inhalation therapy.

It is highly desirable that the aerosols should have a particle size less than about 10 microns and preferably less than 5 microns, for example between 0.5 and 3 microns, to ensure effective distribution to very narrow bronchioles. Preferably, administration is by means of devices enabling controlled quantities of the active ingredients to be administered, for example by means of the metered valves hereinbefore mentioned.

The following Examples illustrate pharmaceutical compositions according to the invention.

EXAMPLE 6

16-Methylene-$PGF_{2\alpha}$ (500 μg.) was dissolved in ethanol (1 ml.) and the solution obtained was added to an aqueous solution (12 ml.) containing sodium carbonate (50 mg.). Aqueous sodium chloride solution (0.9% w/v, 2ml.) was then added to give a final volume of 15 ml. The solution was then sterilized by passage through a bacteria-retaining filter and placed in 1.5 ml. portions in 5 ml. ampoules, to give 50 μg. of 16-methylene-$PGF_{2\alpha}$ (in the form of its sodium salt) per ampoule. The contents of the ampoules were freeze-dried and the ampoules sealed. The contents of an ampoule in a suitable volume, e.g. 2 ml., of sterile water or physiological saline gave a solution ready for administration by injection.

EXAMPLE 7

16-Methylene-$PGE_2$ methyl ester (20 mg.) was dissolved in ethanol (10 ml.), mixed with mannitol (18.5 g.), sieved through a 30-mesh sieve, dried at 30°C. for 90 minutes and again sieved through a 30-mesh sieve. Aerosil (microfine silica; 200 mg.) was added and the powder obtained was machine-filled into one hundred No. 2 hard gelatin capsules to give capsules each containing 200 μg. of 16-methylene-$PGE_2$ methyl ester, which after swallowing of the capsules is released into the stomach.

What we claim is:

1. A compound of the formula:

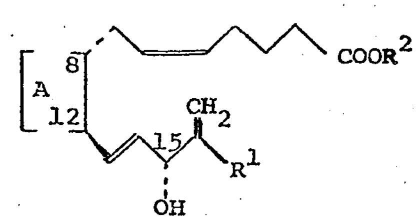

wherein A represents a grouping of the formula:

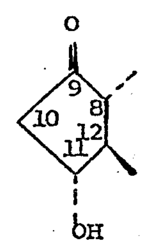

$R^1$ represents a hydrogen atom or a straight- or branched-chain aliphatic hydrocarbon group containing from 1 to 6 carbon atoms, and $R^2$ represents a hydrogen atom or a straight- or branched-chain alkyl group containing from 1 to 12 carbon atoms and cyclodextrin clathrates thereof and, when $R^2$ represents a hydrogen atom, non-toxic salts thereof.

2. A compound according to claim 1 wherein $R^1$ represents a straight- or branched-chain alkyl group containing from 1 to 6 carbon atoms, and A and $R^2$ are as defined in claim 1.

3. A compound according to claim 2 wherein $R^1$ represents the n-butyl group, and A and $R^2$ are as defined in claim 1.

4. A compound according to claim 1 which is 16-methyleneprostaglandin $E_2$ methyl ester and cyclodextrin clathrates thereof.

* * * * *